United States Patent [19]

Cheng

[11] Patent Number: 5,234,815

[45] Date of Patent: Aug. 10, 1993

[54] MONOCLONAL ANTIBODIES AGAINST CYTOSOLIC THYROID HORMONE BINDING PROTEIN

[75] Inventor: Sheue-yann Cheng, Potomac, Md.

[73] Assignee: The United States of America as represented by the Department of Health and Human Services, Washington, D.C.

[21] Appl. No.: 657,943

[22] Filed: Feb. 21, 1991

Related U.S. Application Data

[63] Continuation of Ser. No. 255,760, Oct. 11, 1988, abandoned.

[51] Int. Cl.$^5$ ............................................ G01N 33/53
[52] U.S. Cl. .............................. 435/7.23; 435/240.27; 435/810; 435/975; 435/7.21; 530/806; 530/388.2; 530/388.85; 436/548
[58] Field of Search ...................... 435/7.1, 7.23, 7.21, 435/240.27, 810, 975; 436/548, 808; 935/102, 110; 530/387, 806

[56] References Cited

PUBLICATIONS

Sevier et al, Clin. Chem., vol. 27, No. 11, 1981, "Monoclonal Antibodies in Clinical Immunology", pp. 1797-1806.

Cheng et al, Chem. Abstracts, vol. 104, 1986: 125326h, "Purification and Characterization of a Membrane-Associated 3,3'5-Triiodo-L-Thyronine Binding Protein From a Human Careinoma Cell Line".

Hasumura et al. Chem Abstracts, vol. 105, 1986:223287m, Characterization of a Membrane-Associated 3,3'5-Triiodo-L-Thronine Binding Protein by Use of Monoclonal Antibodies.

Obata et al. Chem. Abstracts, vol. 108, 1988, 183171x, "Antibodies Against the Human Cellular 3,3'5-triiodo-L-Thuronine-Binding Protein" (p. 58).

Primary Examiner—Christine Nucker
Assistant Examiner—Laurie Scheiner

[57] ABSTRACT

Antibodies having specific binding affinity for substantially pure, isolated, thyroid hormone binding protein (p58) are described.

9 Claims, 6 Drawing Sheets

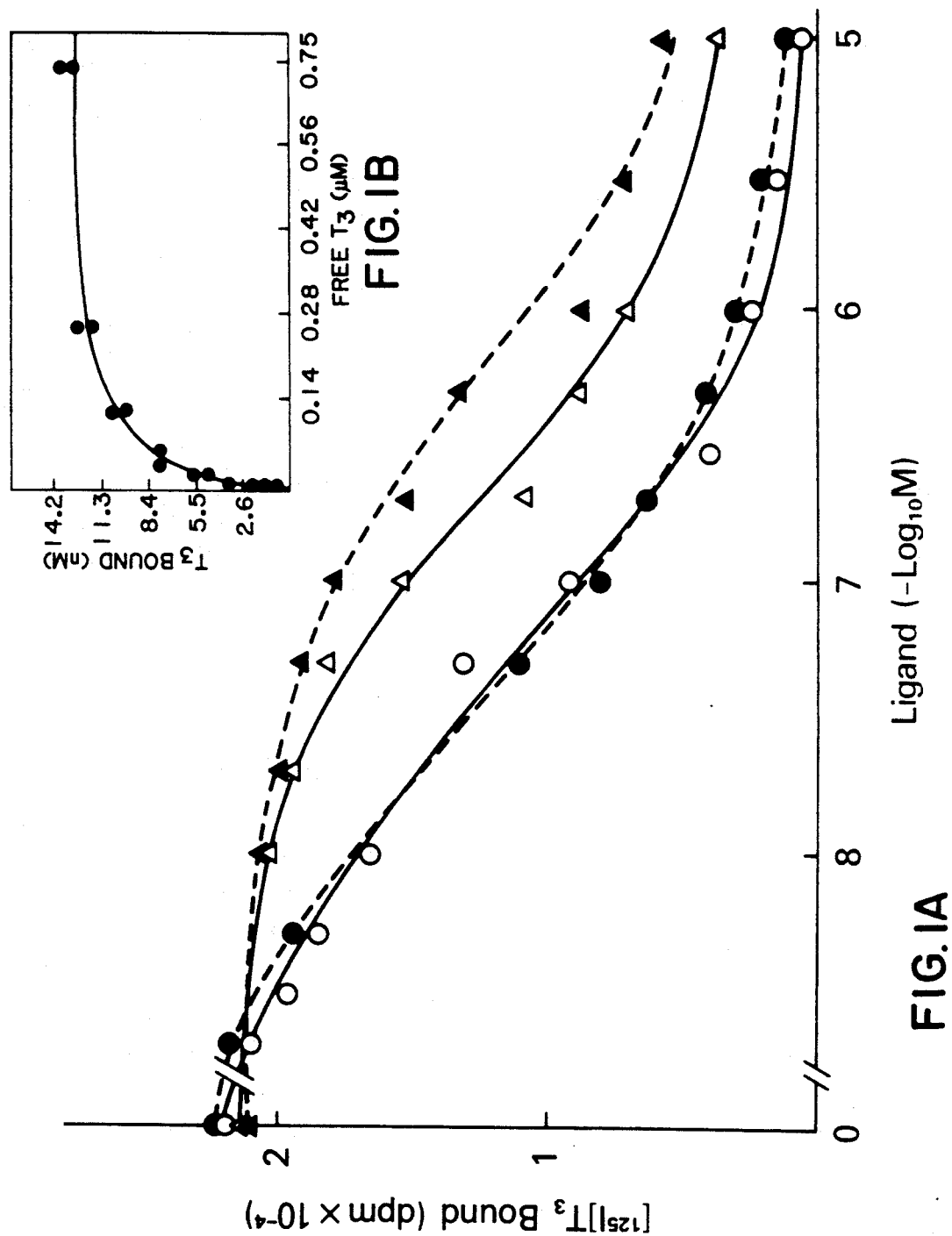

FIG.4A
FIG.4B
FIG.4C

MONOCLONAL ANTIBODIES AGAINST CYTOSOLIC THYROID HORMONE BINDING PROTEIN

This is a continuation of application Ser. No. 07/255,760, filed Oct. 11, 1988 now abandoned.

The present invention is related generally to the preparation of specific antibodies. More particularly, the present invention is related to the preparation of monoclonal antibodies (mAB) having specific binding affinity for a cytoplasmic thyroid hormone binding protein. Heretofore, not even polyclonal antibodies to the cytosolic thryroid hormone binding protein existed. It is noted that unless qualified otherwise, the terms J11 and J12 as used herein mean monoclonal antibodies J11 and J12 produced by hybridomas HB10759 and HB10760, respectively.

SUMMARY OF THE INVENTION

It is, therefore, an object of the present invention to provide monoclonal antibodies which recognize and distinguish cytosolic thyroid hormone binding protein (p58) of different origin.

Other objects and advantages will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein.

Cellular extracts from cultured cells of different species (1–2×10$^5$ cells/60 mm dish) were extracted with 3 mM CHAPS, and 25 ug of cellular extracts were immunoprecipitated with J11 or J12. Lanes 1 and 9; A431, 2 and 10: MCF-7; 3 and 11: HepG2; 4 and 12: KB; 5 and 13: Vero; 6 and 14: CHO; 7 and 15: GH$_3$, 8 and 16: 3T3 cells.

Figure 2A:
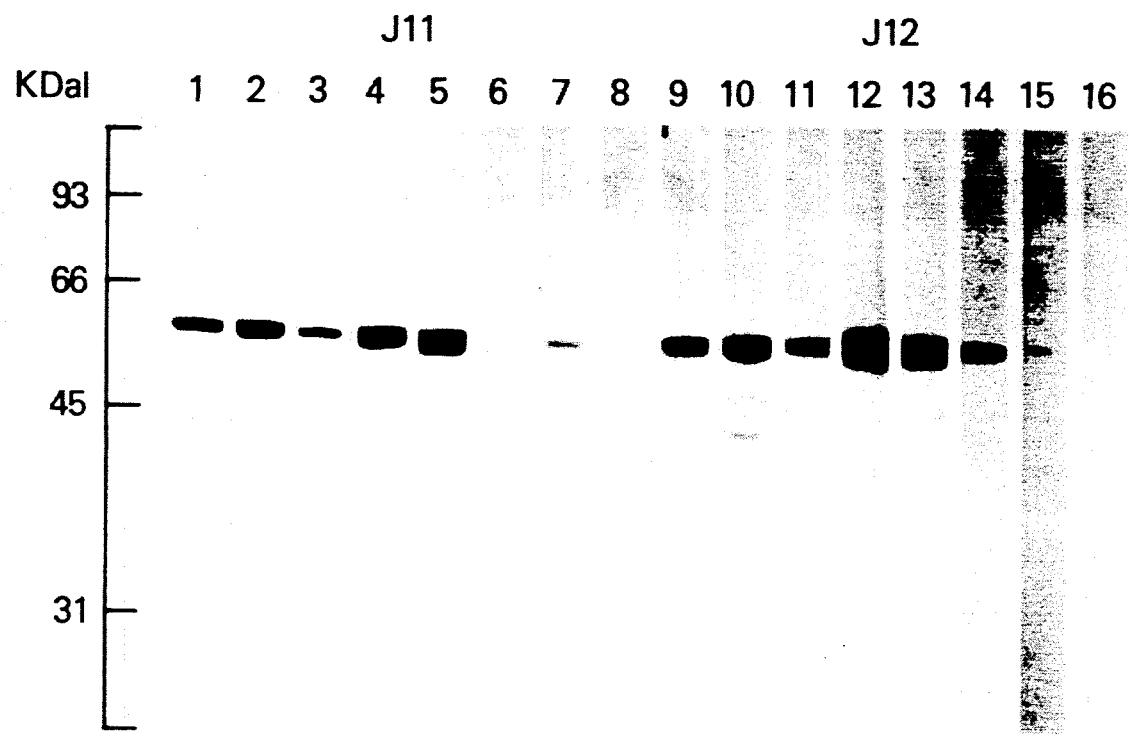
FIG. 2A: Autoradiogram of immunoprecipitates from [$^{35}$S]methionine-labeled CHAPS extracts.
Figure 2B:
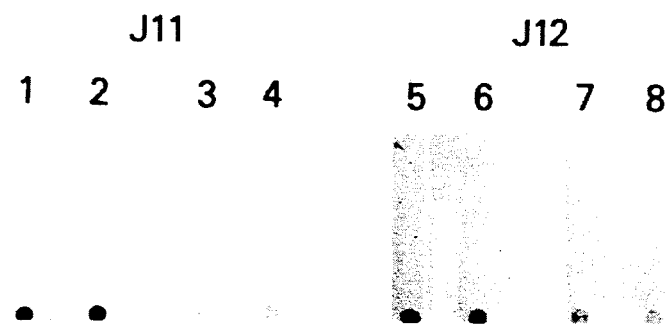

FIG. 2B shows the results of strip-comb dot immunobinding of p58 to J11 or J12.

Purified p58 (10 ng) was spotted onto the tips of strip combs. After drying, the combs were incubated with 50 ul of J11 (1,2) or J12 (5,6) supernatant or negative control medium (3,4,7 and 8). The washing, blocking and color developing was carried out as described in the text.

Figure 3:
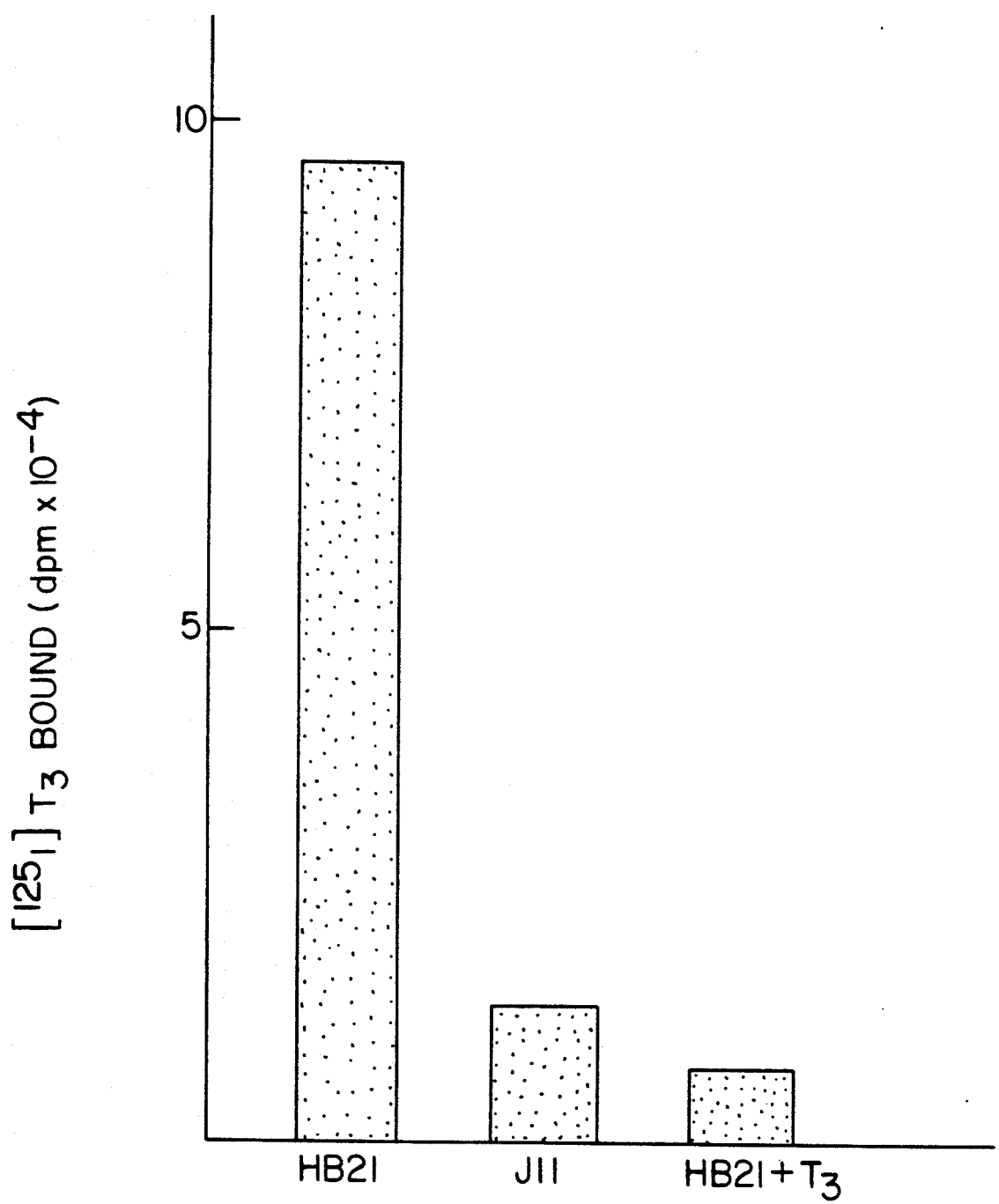

FIG. 3 shows the reduction of T$_3$ binding activity by absorption with J11.

Purified p58 (0.4 ug) was reincubated with 5 ug of the affinity purified J11 or HB21 (anti-human transferrin receptor antibody) in 0.5 ml of binding buffer. After removal of the immune complex by Staph A, the remaining supernatant was incubated with 0.2 nM [$^{125}$I]T$_3$ in the presence or absence of 20 uM T$_3$. The bound radioactivity was separated by a G-25/PD-10 column.

FIG. 4: Immunocytochemical localization of p58 using monoclonal antibody J11.

A431 cells in culture dishes were fixed in situ in formaldehyde (A,B) or using the EGS fixation protocol (c). The cells were subsequently incubated with monoclonal antibody J11 (B,C) or a control non-reactive monoclonal antibody (a) in the presence of saponin. The cells were then further incubated in a rhodamine-antimouse IgG conjugate (A,B) or with the steps of the ferritin bridge method (C). The immunofluorescence pattern shown in (B) is typical of a diffuse distribution in the non-membranous cytoplasm, although increased levels at the margins of membranous elements cannot be completely ruled out. Note the lack of labeling in the nucleus (n), the dark areas representing lack of labeling in large cytoplasmic organelles (B, arrows) and the labeling of ruffles at the cell margin (B, white arrowheads). By electron microscopy (C), the ferritin labeling (arrowheads show examples) shows large amounts of p58 in the cytosolic compartment, with no label detected on the lumenal side of the endoplasmic reticulum (er), in mitochondria (m), or in the nucleus (N). (Mags: A,B = ×700, bar = 10 u; C = ×79,000, bar = 0.1 u).

FIG. 5: Degradation rate of p58.

Figure 5B:
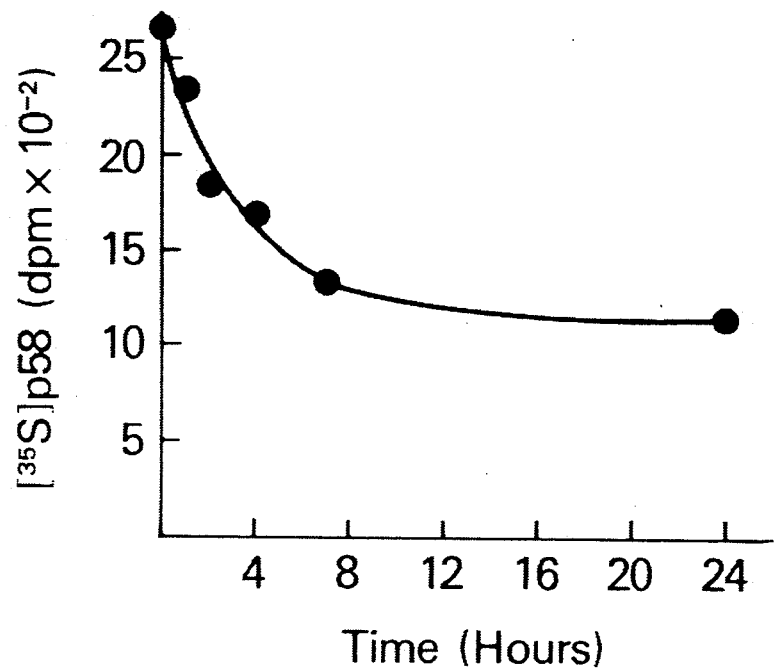
Figure 5A:
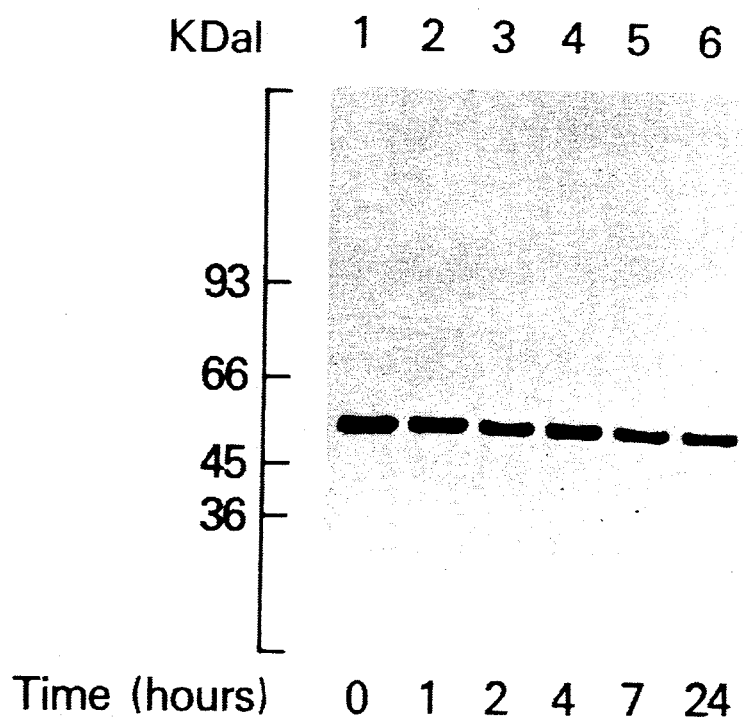

FIG. 5A A431 cells (6.8×10$^5$ cells/60 mm dish) were incubated with [$^{35}$S]methionine (0.5 mCi/ml) for 15 min. The dishes were cooled to 4° C. and washed with 1 ml of 4 mM methionine. The cells were incubated in serum-containing medium for 0 (lane 1), 1 (lane 2), 2 (lane 3), 4 (lane 4), 7 (lane 5) and 24 (lane 6) hours. p58 was extracted and immunoprecipitated with J11. FIG. 8B The radioactive bands at various time points were quantitated by densitometry, and the decay curve was plotted by computer fitting using the equation y = A + Be$^{-kt}$ where y is the total activity at time t, A is the activity at 24 h, B is the activity at time t, k is the rate constant, and t1/2 = 0.693/k.

DETAILED DESCRIPTION OF THE INVENTION

The above and various other objects and advantages of the present invention are achieved by monoclonal antibodies which specifically recognize and distinguish between cytosolic thyroid hormone binding protein (p58) originating from different animal species.

Unless defined otherwise, all technical and scientific terms used herein have the same meaning as commonly understood by one of ordinary skill in the art to which this invention belongs. Although any methods and material similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art.

MATERIALS AND METHODS

Materials

[$^{125}$I]T$_3$. (2200 Ci/mmol), carrier-free [$^{32}$P]phosphoric acid and [$^{35}$S]sulfate were purchased from Dupont New England Nuclear. 3-[(3 cholamidopropyl)-dimethylammonio]-1-propanesulfonate(CHAPS), sodium salts of T$_3$, D-T$_3$ and L-T$_4$, phenylmethanesulfonyl fluoride, aprotinin, and leupeptin were from Sigma. Endoglycosidase H and N-glycanase were purchased from Genzyme Corp. (Boston, MA). [$^{35}$S]Methionine (1200 Ci/mmol) was from Amersham; tunicamycin was from Calbiochem. Dulbecco's modified Eagle's medium was from Gibco; hypoxanthine/aminopterin/thymidine was obtained from Bethesda Research Laboratory. Heat-inactivated fetal bovine serum and Iscor's (modified) Dulbecco's medium were from Hazleton Dutchland, Inc. Affinity-purified rabbit and goat anti-mouse (H and L chain) antibodies were from Jackson Immunoresearch, Inc. Polyethylene glycol (Mr 3000-3700) was from T.J. Baker Co.

Cell Lines

A431, GH$_3$, mouse 3T3 and Chinese hamster ovary cells were propagated as described by Cheng (1983) *Endocrinology* 112, 1754-1762. Human KB, HepG2, dog MDCK and monkey Vero cells were obtained from American Type Culture Collection (Rockville, MD). MCF-7 cells were provided by Dr. R. Evans of the Salk Institute for Biological Studies.

Purification of the T$_3$-Binding Protein from A431 Cells p 58 was purified from A431 cells as described by Kitagawa et al (1987) *J. Biol. Chem.* 262, 3903-3908, except for the following modification. After QAE ion exchange column chromatography the flow-through (about 90 ml) was concentrated to about 20 ml by ultra-filtration (PM-30) and dialyzed against 1-2 L of buffer D (50 mM NaCl, 20 mM phosphate, 0.5 mM CHAPS and the protease inhibitors: 1 mM EDTA, 1 ug/ml leupeptin and 0.5 mM phenylmethanesulfonyl fluoride, pH 6.0 for 18-20 hrs with three changes at 4° C. After dialysis, the dialysate was applied to a SP-Sephadex C-50 column (1.2×8.8 cm) which was pre-equilibrated with buffer D. After washing with 50 ml of buffer D, p58 was eluted with 50 ml to 100 mM phosphate, pH 6.5 at a flow rate of 50 ml/hr. The T$_3$-binding fractions were pooled (20 ml) and diluted with three volumes of buffer E (10 mM phosphate, 0.5 mM CHAPS and the same protease inhibitors as in buffer D, pH 6.8). The pooled fractions were applied to a hydroxylapatite column (0.9×6 cm) which was pre-equilibrated with buffer E. The column was washed successively with 15 ml of 30 mM phosphate, 5 ml of 50 mM phosphate, 20 ml of 65 mM phosphate and 20 ml of 70 mM phosphate. The T$_3$-binding activity was eluted with 30 ml of 80 mM phosphate followed by 10 ml of 120 mM phosphate at a flow rate of 10 ml/hr. The purity of p58 was examined by 10% SDS-PAGE. Compared with the method used before (Kitagawa et al, supra), the yield in this simplified protocol is increased by 3-4 fold from about −50 ug to about −200 ug/2.5×10$^9$ cells. Furthermore, the specific activity of the purified protein is also increased by about 2 fold from (37.6±12.5) to (90.1±1.5) fmole T$_3$-bound/ug protein.

Binding Assay

Binding assays were carried out by incubating the CHAPS extract or purified protein with 0.2 nM [$^{125}$I]T$_3$ for 30 min at 4° C. Protein-bound [$^{125}$I]T$_3$ was separated from unbound radioligand on a Sephadex G-25 (medium column as described by Bolger, et al, (1980) *J. Biol. Chem.* 255, 10271-10278. Binding data were analyzed by least squares analysis as described in Horiuchi et al, supra.

Production of Monoclonal Antibodies

Immunization, Fusion and Cloning

Mice were immunized with purified p58 using a particular protocol as described in Obata et al(FEBS Letters, 230:9-12). The last boost (5 ug of purified p58 in 0.5 ml phosphate-buffered saline) was administered half by intraveneous and half by intraperitoneal injection 72 hrs before fusion. Splenocytes from the immune mice were fused with p3x 63Ag8653 myeloma cells by using the methods described by Liang, et al, (1985) *Biochem. Biophys. Res. Commun.* 128, 171-178. The positive hybridomas were identified by (a) ELISA; (B) Strip-comb dot immunobinding according to Obata, et al, (1988) *Biotechniques* 6:299-302; (c) Immunoprecipitation of the [$^{35}$S]Methionine-labeled lysate of A431 cells as described by Obata, et al (1988) *FEBBS Lett.* supra. The hybridomas were cloned by the standard limiting dilution method.

A deposit of the hybridomas that produce mABs J11 and J12 has been made at the ATCC on May 23, 1991 under accession numbers HB 10759 and 10670, respectively. The deposit shall be viably maintained, replacing if it becomes non-viable during the life of the patent, for a period of 30 years from the date of the deposit, or for 5 years from the last date of request for a sample of the deposit, whichever is longer, and upon issuance of the patent made available to the public without restriction in accordance with the provisions of the law. The Commissioner of Patents and Trademarks, upon request, shall have access to the deposit.

Degradation Rate of p58 in A431 Cells

The degradation rate of p58 was evaluated by pulse-chase experiments as described in Hasumura, et al (1986) *Biochemistry* 25, 7881-7888. After pulsing the cells with [$^{35}$S]methionine for 15 min, the medium was aspirated. The cells were cultured in Dulbecco's modified Eagle's medium containing 10% fetal calf serum and cells were harvested at intervals of 0, 1, 2, 4, 7 and 24 hrs. Immunoprecipitation of cellular extracts was carried out as described in Obata, et al, supra. The immunoprecipitated bands were quantitated by densitometry.

Post-Translational Modification of p58 in A431 Cells

(I). Tunicamycin Experiment

A431 cells (3×10$^6$ cells/100 mm dish) were preincubated with 10 ug/ml tunicamycin at 37° C. for 5 hr. [$^{35}$S]methionine (1 mCi/dish) was added and incubated for 3 hr at 37° C. At the end of the incubation, cells were washed and harvested with a rubber policeman. Preparation of cellular extracts and immunoprecipitation with J11 were carried out as described in Hasumura, et al, supra. Inhibition in the incorporation of carbohydrate moieties into the receptor for epidermal growth factor was used as a positive control. Under these conditions and using Ab 2913 for immunoprecipitation, receptor for epidermal growth factor migrated as bands with molecular weights of −133,000 and −75,000 in contrast to the intact molecule with a molecular weight of 170,000.

(II). Digestion of the Purified p58 with N-Glycanase and Endoglycosidase H

The digestion of the purified p58 (5-10 ug) by either enzyme was carried as described in Hasumura, et al, supra. Ovalbumin (1 ug) was used as a positive control. At the end of digestion, the enzymatic mixture was analyzed by 10% SDS-PAGE followed by Coomassie blue staining.

(III). Phosphorylation and Sulfation Experiments

A431 cells ($3 \times 10^5$ cells/60 mm dish) were incubated with [$^{32}$P]phosphoric acid (2.5 mCi/dish) in phosphate-free or with [35S]Sulfate (1 mCi/dish) in sulfate-free medium for 2, 4, 6 or 24 hrs. The medium was removed, and cells were washed with PBS. CHAPS extracts were prepared and immunoprecipitated following standard methodology.

Localization of p58 by Subcellular Fractionation

Overnight cultures of A431 cells ($1 \times 10^7$ cells/150 mm dish) were washed with 30 ml of PBS (Ca++ and Mg++ free). Cells were harvested with a rubber policeman and pelleted. The cell pellet was resuspended in 2 ml of homogenization buffer (0.25M sucrose, 20 mM Tris, 1.1 mM MgCl$_2$, pH 7.85) and homogenized in a tight dounce homogenizer. After centrifugation at 800 xg for 10 min, the supernatant was further centrifuged at 110,000 xg for 90 min at 4° C. (supernatant A). The pellet was resuspended by pipetting in 1 ml of the homogenizing buffer. The suspension was centrifuged at 110,000 xg for 90 min (supernatant B). The pellet was extracted with 1 ml of 3 mM CHAPS by stirring for 30 min. The suspension was centrifuged at 110,000 xg for 90 min (supernatant C). T$_3$ binding was carried out by using 50 ug of protein from supernatant A, B and C.

In a separate experiment, A431 cells ($5 \times 10^6$ cells/100 mm Dish) were labeled with [$^{35}$S]methionine for 20 hrs at 37° C. Similar cell fractionation was carried out. 25 ug of protein from supernatant A, B and C were immunoprecipitated with J11.

Immunocytochemistry

A431 cells, as well as other cell types, in 35 mm plastic dishes were fixed using 3.7% formaldehyde for 10 min at room temperature (about 22°-25° C.), washed in PBS and then incubated in primary mouse monoclonal antibodies at 10 ug/ml in a diluent composed of 4 mg/ml normal goat globulin, 0.1% saponin, PBS (NGG-sap-PBS) as described in Willingham, et al, (1985) *An Atlas of Immunofluorescence in Cultured Cells*, Academic Press, Orlando, FL, pp. 1-13. The cells were incubated in this step for 30 min at 23° C., washed in PBS and then incubated with rhodamine labeled affinity-purified goat anti-mouse IgG (Jackson ImmunoResearch) (50 ug/ml in NGG-sap-PBS for 30 min, 23° C.). The cells were washed and mounted under a coverslip in buffered glycerol. Other experiments were performed using permeabilization with 0.1% Triton X-100 for 5 minutes at 23° C., or 80% acetone treatment for 5 min after the formaldehyde fixation step.

For electron microscopic immunocytochemistry, A431 cells were fixed in plastic dishes using the EGS procedure with 0.17% glutaraldehyde, and labeled using the ferritin bridge method described in Willingham (1980) *Histochem. J.* 12, 419-434. The steps of the ferritin bridge sequence included: 1) mouse monoclonal antibodies (J11) or non-reactive control mouse monoclonal; 10 ug/ml; 2) goat anti-mouse IgG (1:20 diluted whole IgGO, 3) affinity-purified mouse anti-ferritin (Jackson ImmunoResearch; 50 ug/ml) and 4) house spleen ferritin (200 ug/ml). The cells were then post-fixed in glutaraldehyde and osmium, and embedded in situ (Willingham (1980) supra. Quantitation was performed by measuring demarcated areas of extra-membranous cytoplasm in random prints of the same magnification using the MacMeasure program (Hook, et al, (1987) *Proc. 45th Annual Meeting of Electron Microscopy Society of America*, p. 920) with a MacPlus TM computer. The numbers of ferritin cores in these areas were counted and assuming a section thickness of 1000 A, the levels of p58 localization were calculated as number of ferritin cores per u$^3$ extramembranous cytoplasm (cytosol). This data is presented in Table II.

RESULTS

Binding of T$_3$ and Its Analogs to Purified p58

Figure 1:
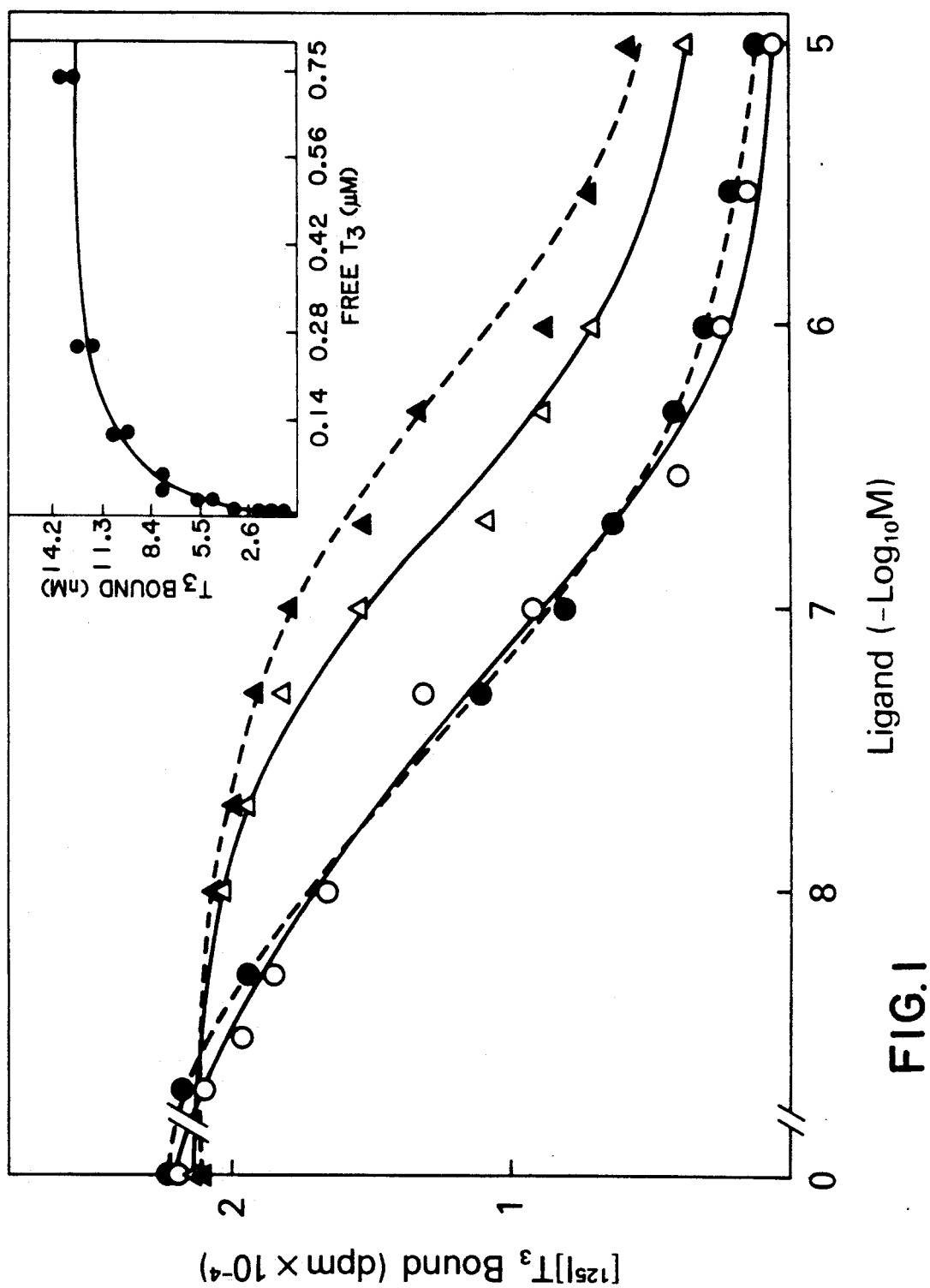
FIG. 1A shows the results of the studies of thyroid hormone binding to purified p58. Purified p58 (0.4 ug) was incubated with 0.2 nM [$^{125}$I]T$_3$(o), T$_4$(●), D-T$_3$(⊕) or reverse-T$_3$(▲) for 0.5 hr at 4° C. At the end of incubation, free and bound [$^{125}$I]T$_3$ was separated.
FIG. 1B The data from T$_3$ binding was replotted as bound vs. total free T$_3$. The line is the theoretical curve calculated from equation as described in Horiuchi et al (1982) *Proc. Natl. Acad. Sci. USA* 79, 5527–5531.

FIG. 1A shows the binding of [$^{125}$I]T$_3$ to purified p58 with increasing concentrations of unlabeled T$_3$, T$_4$, D-T$_3$ and reverse-T$_3$ under equilibrium conditions. T$_3$ and T$_4$ bind to p58 with similar affinity. However, D-T$_3$ and reverse-T$_3$ bind to p58 with an affinity 4- and 10-fold less than that of T$_3$, respectively.

The inset in FIG. 1B shows a plot of T$_3$ bound vs. increasing free T$_3$ concentration. The line is the theoretical curve calculated from the equation described in Horiuchi, et al, supra. The data fit the calculated curves to give one class of binding sites with a Kd=24.3±0.3 nM and n=0.71 (moles T$_3$ bound per mole of p58). Earlier, the Kd for the binding of T$_3$ to p58 in the cellular extract was found to be 17±3 nM. These results indicate that the binding activity of p58 is stable under the conditions used for purification.

Characterization of Monoclonal Antibodies Against p58

Purified p58 which retains T$_3$ binding activity was used as an immunogen to produce antibodies. Using a special immunization protocol as described herein, supra, hybridomas HB 10759 and HB 10760, were found to secrete antibodies J11 and J12, respectively that immunoprecipitated a 58k protein in A431 cells (lanes 1 and 9 in FIG. 2A). Furthermore, as shown in FIG. 2B, both antibodies reacted with purified p58 as shown using strip-comb dot immunobinding.

To determine the species specificity of J11 and J12 and to compare the abundance of p58 in different culture cell lines, p58 was extracted and immunoprecipitated by both antibodies. As shown in FIG. 2A and Table I, both antibodies recognize p58 from human, monkey, dog and rat. None of the two antibodies recognizes p58 from mouse. J12 recognizes p58 from hamster; but J11 does not. Furthermore, comparison of the relative intensity of the bands showed that KB cells, a carcinoma cell line, have the highest abundance of p58. It was further found that J12 has a higher affinity for human p58, but is less reactive to rat p58 than J11. These results clearly indicate that J11 and J12 are not the same mAB and do not recognize the same epitopes on p58.

Immunodepletion experiments were also carried out to see whether T$_3$ binding activity of purified p58 can be recognized by J11 and J12. p58 was first reacted with J11 or J12. The immunocomplex was precipitated by Staph A. The binding activity in the supernatant was examined as shown in FIG. 3. When HB21, a monoclonal antibody against the human transferrin receptor was used, $\sim 1 \times 10^5$ dpm of [$^{125}$I]T$_3$ binding activity was detected in the supernatant. This binding activity was specific, since in the presence of 20 uM of unlabeled T$_3$, only 5% of activity remained. However, J11 removed 90% of this $T_3$ binding activity from the supernatant. J12 gave similar results (data not shown). These results indicate that J11 and J12 recognized the component responsible for the observed $T_3$ binding activity. Thus, it is clear that the $T_3$ binding activity resides in p58 and the binding activity does not derive from a trace contaminant present in the p58 preparation.

To determine the class and subclass of the antibodies, the clones were labeled with [$^{35}$S]methionine; the culture supernatants were harvested and immunoprecipitated with affinity-purified rabbit anti-mouse IgG subclass specific antibodies. Both J11 and J12 were found to be IgG$_1$k antibodies.

Immunocytochemical Localization of p58

Cultured cells were fixed and permeabilized for immunofluorescence. Following formaldehyde fixation and permeabilization with either saponin, acetone or Triton X-100, the cells showed a bright pattern of fluorescence confined to the extramembranous cytoplasm as shown in FIG. 4B. Both J11 and J12 showed identical patterns in A431 cells. No localization was seen in the interior of the nucleus under any of these fixation permeabilization conditions. Typical of such a cytosolic pattern, surface ruffles showed bright localization and larger cytoplasmic organelles could be seen as dark areas of exclusion in the cytoplasm. The species specificity of mAbs J11 and J12 was also evaluated using immunofluorescence. As shown in Table I, the results are consistent with the findings by immunoprecipitation.

The localization of p58 was investigated further using electron microscopic immunocytochemistry in A431 cells. As shown in FIG. 4C, the distribution of p58 seen with this approach agreed with the results seen using immunofluorescence, in that all of the localization found was in the extramembranous cytoplasm, with no particular concentration in any one part of the cell. No localization was seen on the external plasma membrane surface or in the nucleus. The cytosolic localization of p58 was then quantitated morphologically as shown in Table II. From these measurements, the minimum number of molecules of p58 present per cell can be estimated (>300,000 molecules per cells). This estimation is consistent with the biochemical estimation in which A431 cells contained $1-2\times10^6$ molecules p58/cell.

Localization of p58 by Subcellular Fraction

To identify the subcellular localization of p58 biochemically, A431 cells were homogenized under isotonic conditions. After removal of unbroken cells and nuclei, the 110,000 xg supernatant was prepared. After washing the pellet once with the homogenization buffer, the pellet was further extracted with 3 mM CHAPS. Table III shows that 94–97% of $T_3$ binding activity and J11 immunoreactivity are present in the 110,000 xg supernatant. These results are consistent with the findings by morphological methods that p58 is located in cytosol. The 3–6% $T_3$ binding activity that remained with the 110,000 xg pellet may be due to p58 trapped in vesicles during homogenization.

TABLE I

| Anti-body | Assay | Reactivity of monoclonal antibodies J11 and J12 with cultured cells of different species | | | | | | | | |
|---|---|---|---|---|---|---|---|---|---|---|
| | | Human | | | | Monkey Vero | Hamster CHO | Rat GH$_3$ | Mouse 3T3 | Dog MDCK |
| | | A431 | KB | HepG2 | MCF-7 | | | | | |
| J11 | Immumo-fluorescence | + | + | + | + | + | − | + | − | + |
| | Immuno-precipitation[a] | 14 | 44 | 5 | 20 | 37 | 0 | 1 | 0 | ND[b] |
| J12 | Immuno-fluorescence | + | + | + | + | + | + | + | − | + |
| | Immuno-precipitation[a] | 22 | 187 | 15 | 46 | 80 | 6 | 0.5 | 0 | ND[b] |

[a]The immunoprecipitation was carried out as described in Methods. An equal amount of protein (25 μg) was used in immunoprecipitation. The intensity of the radioactive p58 bands was determined by densitometry. The values are relative intensity using p58 from GH$_3$ immunoprecipitated by J11 as reference.
[b]N.D. - not determined.

TABLE II

Quantitation of the electron microscopic immunocytochemical localization of p58

| Primary Antibody | Ferritin Cores/μ$^3$ (± S.E.) in Cytosol | Volume Measured (μ$^3$) | Cores Counted |
|---|---|---|---|
| J11 | 1579 ± 188 | 1.20 | 1873 |
| Control | 12 ± 7 | 0.71 | 8 |

Assuming a cytosol volume of $5 \times 10^{-10}$ cm$^3$ (500 μ$^3$), and assuming two ferritin cores indirectly attached to each molecule of p58, the minimum cytosol content of p58 would be: $1579/2 = 783$ molecules/μ$^3$ × 500 μ$^3$ cytosol/cell = 391,500 molecules p58/cell.

TABLE III

| Fraction (110,000 xg) | Specific [$^{125}$I]T$_3$ bound | | J11 immunoreactivity[a] | |
|---|---|---|---|---|
| | dpm(× 10$^{-4}$) | % of total | dpm(× 10$^{-3}$) | % of total |
| Supernatant | 2.5 | 94 | 5.5 | 97 |
| Pellet | 0.17 | 6 | 0.18 | 3 |

[a]Aliquots (25 μg) of supernatant was immunoprecipitated with 1 μg of affinity purified J11. After a 10% SDS-PAGE, the radioactive p58 bands were cut and counted.

In these and earlier preliminary studies, it was found that the $T_3$ binding activity is 3-fold more stable in the presence of 0.5–3 mM CHAPS (data not shown). Therefore, all binding studies and the chromatographic steps were carried out in the presence of CHAPS.

Post-Translational Modification and Turnover of p58

To evaluate whether p58 is post-translationally modified by glycosylation, three different experiments were carried out. A431 cells were pulsed with [$^{35}$S]methionine for 15 min followed by a chase with unlabeled methionine for 1, 2, 4 7 and 24 hrs. FIG. 5A shows the autoradiogram of a SDS-PAGE of the immunoprecipitates using J11. No specific radioactive bands with molecular weight higher than 58K could be detected at all time points examined. These results indicated that within the detection sensitivity of the size change in a 10% gel, p58 is not processed. The p58 bands were quantified by densitometry and the decay curve was plotted. The data fit into a model in which there is a fast decaying component and a stable pool. As shown in FIG. 5B, the fast decaying pool was degraded with $t_{\frac{1}{2}}$ (2.11±1.08) hrs. Medium was collected and assayed for its content of p58 by immunoprecipitation. No detectable p58 was found, thus p58 was not secreted from the cell.

Two additional experiments were also carried out to confirm that p58 is not post-translationally modified. A431 cells were pretreated with tunicamycin for 5 hr, and labeled with [$^{35}$S]methionine for 3 hrs. Cellular extracts were prepared and immunoprecipitated with J11. No difference in the molecular weight of immunoprecipitable bands was observed whether cells were treated with tunicamycin or not (data not shown). These results indicate that p58 is most likely not glycosylated. In addition, purified p58 was treated with N-glycanase or endoglycosidase H. In the same experiment, ovalbumin and transthyretin were treated similarly. The sugar residues were removed from ovalbumin by either enzyme to give a protein band with a molecular weight of −38K, while transthyretin was not affected. Under these conditions, no detection of lower molecular weight species was seen for p58. The results from these three experiments indicate that p58 is not likely to be a glycosylated protein.

To determine whether p58 is post-translationally modified by phosphorylation or sulfation, A431 cells were labeled with [$^{32}$P]phosphoric or [$^{35}$S]sulfuric acid for 1, 2, 4 and 16 hr. Cell lysates were immunoprecipitated with J11. No incorporation of $^{32}$P or $^{35}$S was seen in p58. These results indicate that p58 probably is not a phosphorylated or sulfated protein.

In summary, by using the monoclonal antibodies of the present invention it was demonstrated that the previously isolated cellular thyroid hormone binding protein (p58) is located in the cytosol. Using crude cytosol preparations, a cytosolic binding protein for thyroid hormone has been reported to be present in liver, kidney, red cells, brain, and GH cells. The reported biochemical properties, however, vary greatly. The molecular weights range from 6000 to >100,000; the Kd's of T$_3$ and T$_4$ binding vary from $6.6 \times 10^{-8}$ to $4 \times 10^{-11}$M and $1.2 \times 10^8$ to $2.9 \times 10^{-10}$M, respectively. Furthermore, one and two classes of binding sites for thyroid hormone were also reported (Davis, et al, (1974) *J. Biol. Chem.* 249, 6208–6217). In the present study, using a purified preparation, one class of binding sites with a Kd of 24.3±0.3 nM was found. T$_4$ binds to p58 with an affinity similar to that of T$_3$. These binding characteristics were similar to that reported in the previous studies in which a crude preparation was used (Kitagawa, et al, supra).

A question frequently raised is the structural relationship between the cytosolic binding protein and nuclear receptors for T$_3$. The present study clearly demonstrates that they are structurally unrelated based on the following evidence: (a) Immunofluorescence and morphological studies indicate the p58 is exclusively present in cytosol and not in nuclei. (b) T$_3$ binding activity of p58 can be absorbed by J11 and J12, whereas the T$_3$ binding activity of nuclear extracts of A431 cells cannot be removed by J11 and J12 (data not shown). (c) It has been reported that c-erb-A protein is the T$_3$ nuclear receptor. When the [$^{35}$S]methionine-labeled in vitro translation products of human placental c-erb-A were incubated with J11 or J12, no immunoprecipitable bands were detected (data not shown). When the in vitro translation product of human placental c-erb-A were prepared, comparison of the peptide maps of V8 digestion between p58 and c-erb-A translation products showed no common fragments (data not shown). These results indicate that p58 is distinct from T$_3$ nuclear receptors.

It is clear from the data and the demonstrated species specificity of J11 and J12 mAbs of the present invention with respect to p58, that these antibodies are quite useful in elucidating the localization and biochemical and functional roles of p58 which otherwise would not be possible. Furthermore, these antibodies could also be used to identify cells which are rapidly dividing, such as some tumor cells.

A kit in accordance with the present invention comprises containers separately containing mAbs J11 and J12 in a physiological buffered medium or a biochemically acceptable, nontoxic, sterile carrier.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A monoclonal antibody having specific binding affinity for p58.

2. The monoclonal antibody of claim 1 obtained from a hybridoma selected from the group consisting of HB10759 and HB10760.

3. The monoclonal antibody of claim 2 obtained from hybridoma HB10759.

4. The monoclonal antibody of claim 2 obtained from hybridoma HB10760.

5. A hybridoma producing monoclonal antibody having specific binding affinity for p58.

6. The hybridoma of claim 5 selected from the group consisting of HB10759 and HB10760.

7. The hybridoma of claim 6 being HB10759.

8. The hybridoma of claim 6 being HB10760.

9. A kit comprising containers separately containing monoclonal antibodies J11 and J12.

* * * * *